United States Patent
Perkes

(10) Patent No.: US 6,818,233 B2
(45) Date of Patent: Nov. 16, 2004

(54) DIETARY SUPPLEMENTS CONTAINING NATURAL INGREDIENTS

(75) Inventor: Lynn Perkes, Rexburg, ID (US)

(73) Assignee: Melaleuca, Inc., Idaho Falls, ID (US)

(*) Notice: Subject to any disclaimer, the term of this patent is extended or adjusted under 35 U.S.C. 154(b) by 0 days.

(21) Appl. No.: 09/194,165

(22) PCT Filed: Aug. 5, 1998

(86) PCT No.: PCT/US98/16181
§ 371 (c)(1),
(2), (4) Date: May 11, 1999

(87) PCT Pub. No.: WO99/07400
PCT Pub. Date: Feb. 18, 1999

(65) Prior Publication Data
US 2002/0048575 A1 Apr. 25, 2002

Related U.S. Application Data

(63) Continuation of application No. 08/907,317, filed on Aug. 6, 1997, now abandoned.

(51) Int. Cl.[7] .......................... A61K 35/78; A61K 38/43; A61K 38/54
(52) U.S. Cl. ........................ 424/766; 424/725; 424/752; 424/94.1; 424/94.2
(58) Field of Search .................... 424/725, 766, 424/752, 94.1, 94.2, 94.6, 94.63, 195.1; 514/27

(56) References Cited

U.S. PATENT DOCUMENTS

| | | | |
|---|---|---|---|
| 3,615,721 A | 10/1971 | Silberman | 99/199 |
| 4,393,085 A | 7/1983 | Spradlin et al. | 426/28 |
| 4,698,360 A | 10/1987 | Masquelier | 514/456 |
| 4,737,364 A | 4/1988 | Kalogris | 424/195.1 |
| 5,009,891 A | 4/1991 | Niwa et al. | 424/195.1 |
| 5,308,627 A | 5/1994 | Umbdenstock, Jr. | 424/639 |
| 5,387,422 A | * 2/1995 | Handel et al. | 426/2 |
| 5,484,594 A | 1/1996 | Frangi et al. | 424/195.1 |
| 5,565,435 A | 10/1996 | Yoneyama et al. | 514/27 |
| 5,567,424 A | * 10/1996 | Hastings | 424/195.1 |
| 5,569,458 A | 10/1996 | Greenberg | 424/195.1 |
| 5,589,182 A | 12/1996 | Tashiro et al. | |
| 5,626,849 A | 5/1997 | Hastings et al. | 424/195.1 |
| 5,904,924 A | * 5/1999 | Gaynor et al. | 424/195.1 |
| 5,948,443 A | 9/1999 | Riley et al. | |
| 5,976,568 A | 11/1999 | Riley | |
| 6,030,621 A | * 2/2000 | De Long et al. | 424/195.1 |
| 6,054,128 A | 4/2000 | Wakat | |

OTHER PUBLICATIONS

Indena Pharmaceuticals Natural Active Principals from Medicinal Plants; http://www.indena.it/pharmac.htm, Oct. 2000.*

Balch et al. Prescription for Nutritional Healing; Second edition, pp. 20–21 and 47–48, 1997.*

Revilla et al. Comparison of Several Procedures Used for the Extraction of Anthocyanins from Red Grapes; Journal of Agricultural and Food Chem., (1998), 46 (11) pp. 4592–4597.*

(List continued on next page.)

*Primary Examiner*—Patricia Leith
(74) *Attorney, Agent, or Firm*—Fish & Richardson P.C., P.A.

(57) ABSTRACT

The invention provides a dietary supplement comprising at least one flavonoid source and an enzyme, that is effective for inhibiting in vivo platelet activity and LDL cholesterol oxidation in a mammal at a dosage of about 30 mg/Kg or less. The supplement may contain flavonoid sources found in grape seed extracts, grape skin extracts, bilberry extracts, ginkgo biloba extracts or the flavonoid quercetin. The supplement may also contain fungal proteases, acid stable proteases and bromelain. The invention further provides a method for using the dietary supplement and an article of manufacture containing the supplement.

28 Claims, 8 Drawing Sheets

OTHER PUBLICATIONS

Stedman's Medical Dictionary; definition of 'extract'; 27th Ed.*

Cao et al., "Increases in human plasma antioxidant capacity after consumption of controlled diets high in fruit and vegetables," *Am J. Clin. Nutr.*, 1998, 68:1081–1087.

Dallas et al., "Degradation of oligomeric procyanidins and anthocyanins in a Tinta Roriz red wine during maturation," *Vitis*, 1995, 34(1):51–56.

Folts et al., "Moderate alcohol consumption, CAD, and myocardial ischemia," *J. Myocardial Ischemia*, 1994, 6(8):33–40.

Hashimoto et al., "Effect of Acute Intake of Red Wine on Flow–Mediated Vasodilation of the Brachial Artery," *Am. J. Cardiol.*, 2001, 88:1457–1460.

Morris et al., "Effects of Fruit Maturity, Juice Storage, and Juice Extraction Temperature on Quality of 'Condord' Grape Juice," *J. Amer. Soc. Hort. Sci.*, 1986, 111(5):742–746.

Preuss et al., "Effects of Niacin–Bound Chromium and Grape Seed Proanthocyanidin Extract on the Lipid Profile of Hypercholesterolemic Subjects: A Pilot Study," *J. Med.*, 2000, 31(5 & 6):227–245.

Singleton and Rossi, Jr., "Colorimetry of Total Phenolics with Phosphomolybdic–Phosphotungstic Acid Reagents," *Am. J. Enol. Vitic*, 1965, 16:144–158.

Strong, "Atherosclerosis in the Young: Risk and Prevention," *Hospital Practice*, 1999, pp. 15, 16, and 19.

Strong et al., "Prevalence and Extent of Atherosclerosis in Adolescents and Young Adults," *JAMA*, 1999, 281(8):727–735.

Human Drugs: Melaleuca; Idaho Falls, ID/Knoxville, TN, facility; Warning Letter Bulletin, Jul. 28, 1997, vol. 5, No. 15, ISSN: 1069-4218, Washington Information Source, Newsletter, XP-002216023, Warning Letter No. 97-NSV-08.

Formica and Regelson, "Review of the Biology of Quercetin and Related Bioflavonoids," *Food Chem. Toxicol.*, 1995, 33(12):1061–1080.

E. Bombardelli, *Phytosome®: New Cosmetic Delivery System*, Boll. Chim. Farmaceutico, (Dec. 1991).

Demrow et al., "Administration of Wine and Grape Juice Inhibits in Vivo Platelet Activity and Thrombosis in Stenosed Canine Coronary Arteries", *Circulation*, 91(4):1182–1188 (1995).

Folts, "An In Vivo Model of Experimental Arterial Stenosis, Intimal Damage, and Periodic Thrombosis", *Circulation*, 83(6) Supplement IV, pp. 3–14 (1991).

Folts, "Drugs for the Prevention of Coronary Thrombosis: From an Animal Model to Clinical Trials", *Cardiovascular Drugs and Therapy*, 9:31–43 (1995).

Folts et al., "Moderate alcohol consumption, CAD, and myocardial ischemia", *J. Myocardial Ischemia*, 6(8):33–40 (1994).

Folts et al., "Possible Platelet Thrombi Formation in Dog and Human Femoral Arteries", *Tex. Heart Inst. J.*, 9:19–26 (1982).

Folts, J.D., "Platelet Aggretation in Partially Obstructed Vessels and its Elimination with Aspirin", *Circulation*, 54(3):365–370 (1976).

Eichhorn et al., Spontaneous Alterations in Coronary Blood Flow Velocity Before and After Coronary Angioplasty in Patients With Severe Angina:, *J. Am. Coll. Cardiol.*, 17:43–52 (1991).

Waterhouse et al., "The Phenolic Phytochemicals in Wine, Fruit and Tea: Dietary Levels, Absorption and Potential Nutritional Effects", *Hyper Nutri. Foods*, Ed. Finley et al, Agscience Inc., Auburndale, Fl, pp. 219–238 (1997).

Folts, J.P., "Three glasses of Grape But Not Orange or Grapefruit Juice Inhibit Ex Vivo Platelet Aggregation in Human Volunteers", *J. Am. Coll. Card.*, 29(2) Supplement A:226A (1997) (Abstract 767–3).

Folts et al., "Platelet Inhibitory Effect of Feeding Grape Juice But Not Orange or Grapefruit Juice for Seven Days in Monkeys", *J. Am. Coll. Card.*, 29(2) Supplement A:303A (1997) (Abstract 1006–156).

Folts, J.D., "Flavonoids In Tea But Not Coffee Given By Gastric Tube Inhibit In Vivo Platelet Activity and Thrombus Formation in Stenosed Dog Coronary Arteries", *FASEB J.*, 10(3):A793 (1996).

Folts et al., "Grape Juice But Not Orange or Grapefruit Juice Significantly Inhibits In Vivo Platelet Activity and Thrombosis in Stenosed Canine Coronary Arteries", *J. Am. Coll. Card.*, 29(2) Supp. A:180A (734–5).

Folts, J.D., "Gastric Administration of a Commercial Flavonoid Dietary Supplement Inhibits In Vivo Platelet Activity and Cyclic Flow Reductions in Stenosed Monkey Carotid Arteries", *Circulation*, 92(8) Supp I–489, No. 2336 (1995).

Slane et al., "Platelet Inhibition in Stenosed Canine Arteries by Quercetin and Rutin, Polyphenolic Flavonoids Found in Red Wine", *Clinical Research*, 42(2):162A (1994) (Abstract 162A).

Beretz et al., "Role of cyclic AMP in the inhibition of human platelet aggregation by quercetin, a flavonoid that potentiates the effect of prostacylcin," *Biochem. Pharmacol.*, 1982, 31(22):3597–3600 (abstract only).

Goker et al., "Synthesis and inhibitory activities on platelet aggregation of some flavonoid analogues," *Arzneimittelforschung*, 1995, 45(2):150–155 (abstract only).

Hertog et al., "Dietary antioxidant flavonoids and risk of coronary heart disease: the Zutphen Elderly Study," *Lancet*, 1993, 342(8878):1007–1011 (abstract only).

Hladovec, "Antithrombotic effects of some flavonoids alone and combined with acetylsalicylic acid," *Arzneimittelforschung*, 1977, 27(10):1989–1992 (abstract only).

Huang et al., "Antiproliferative effect of baicalein, a flavonoid from a Chinese herb, on vascular smooth muscle cell," *Eur. J. Pharmacol.*, 1994, 251(1):91–93 (abstract only).

Jahromi and Ray, "Antihyperlipidemic effect of flavonoids from *Pterocarpus marsupium*," *J. Nat. Prod.*, 1993, 56(7):989–994 (abstract only).

Keli et al., "Dietary flavonoids, antioxidant vitamins, and incidence of stroke: the Zutphen study," *Arch. Intern. Med.*, 1996, 156(6):637–642 (abstract only).

Knekt et al., "Flavonoid intake and coronary mortality in Finland: a cohort study," *BMJ*, 1996, 312(7029):478–481 (abstract only).

Littlewood et al., "Red wine contains a potent inhibitor of phenolsulphotransferase," *Br. J. Clin. Pharmacol.*, 1985, 19(2):275–278 (abstract only).

Monforte et al., "Biological effects of hesperidin, a Citrus flavonoid. (note II): hypolipidemic activity on experimental hypercholesterolemia in rat," *Farmaco*, 1995, 50(9):595–599 (abstract only).

Robak et al., "On the mechanism of antiaggregatory effect of myricetin," *Pol. J. Pharmacol. Pharm.*, 1988, 40(3):337–340 (abstract only).

Smith et al., "The neuroprotective properties of the *Ginkgo biloba* leaf: a review of the possible relationship to platelet-activating factor (PAF)," *J. Ethnopharmacol.*, 996, 50(3):131–139 (abstract only).

Taussig and Batkin, "Bromelain, the enzyme complex of pineapple (*Ananas comosus*) and its clinical application. An update," *J. Ethnopharmacol.*, 1988, 22(2):191–203 (abstract only).

Vellini et al., "Possible involvement of eicosanoids in the pharmacological action of bromelain," *Arzneimittelforschung*, 1986, 36(1):110–112 (abstract only).

* cited by examiner

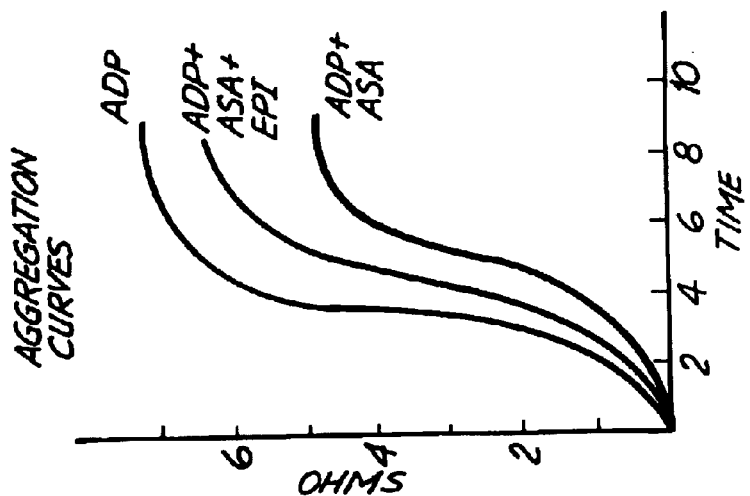
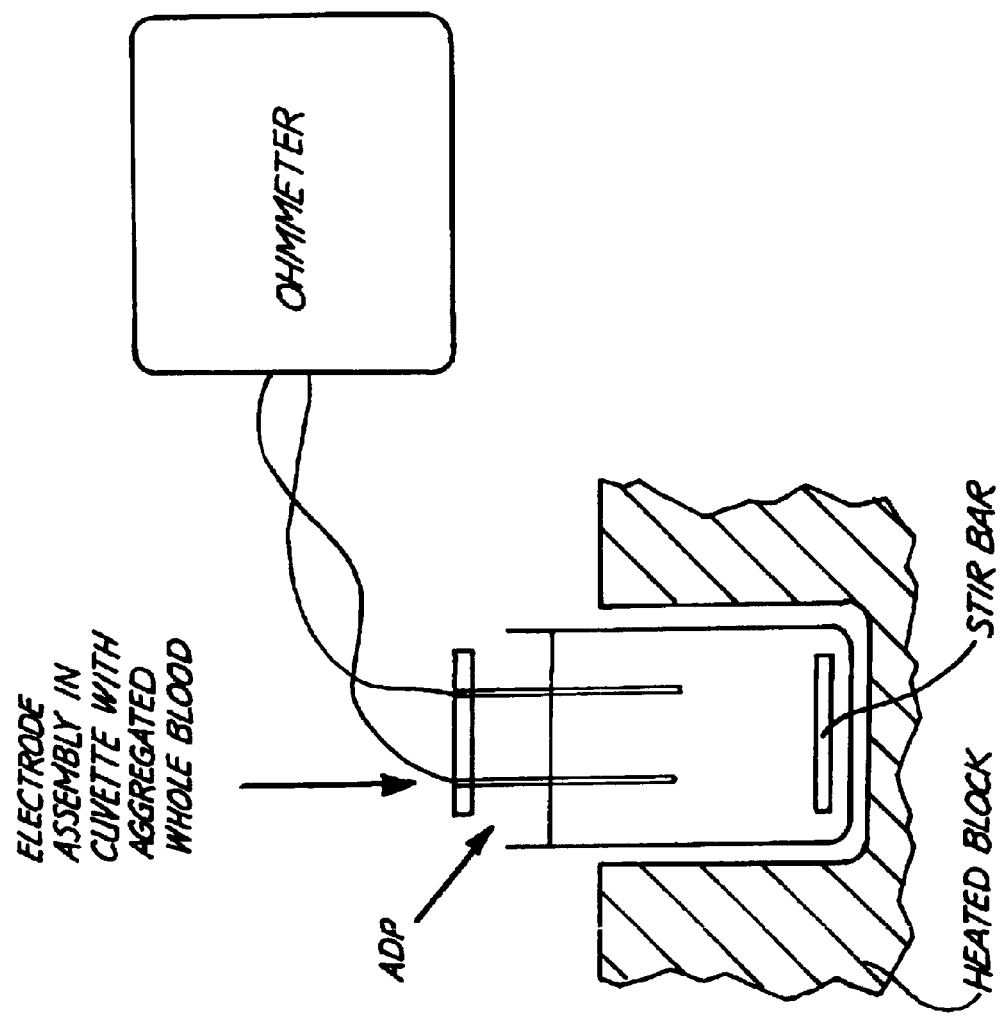
Fig. 5

DIETARY SUPPLEMENTS CONTAINING NATURAL INGREDIENTS

RELATED APPLICATIONS

This application is a U.S. National Phase application of PCT Patent Application No. PCT/US98/16181, filed Aug. 5, 1998, which is a continuation of U.S. patent application Ser. No. 08/907,317, filed Aug. 6, 1997, now abandoned.

BACKGROUND

1. Technical Field

The invention relates to dietary supplements containing natural ingredients.

2. Background Information

Coronary artery disease, myocardial infarction, stroke, and other vascular occlusions are major health concerns. A common characteristic of these diseases is the atherosclerotic process, or the narrowing of arteries. Blood platelets contribute to the development and progression of the atherosclerotic process by releasing growth factors, chemotactic substances and other factors that accelerate the atherosclerotic process. In addition, platelet aggregation at or near the point of arterial damage contributes to the development of atherosclerosis and acute platelet thrombus formation.

Low density lipoprotein (LDL) cholesterol is also associated with atherosclerosis. It has been proposed that non-atherogenic LDL cholesterol circulating in the blood is converted to atherogenic LDL cholesterol through oxidation of polyunsaturated lipids, which leads to modification of the apoprotein.

Physicians use various drugs, such as aspirin, to treat atherosclerotic conditions. Aspirin, however, is not without negative side effects including gastrointestinal irritation. Interventions such as angioplasty are also available to dilate stenosed arteries thereby increasing blood flow. Interventional techniques, however, produce intimal and medial artery damage and expose thrombogenic surfaces. As such, restenosis and the incidence of sudden coronary death following angioplasty is a major concern for patients with known or suspected coronary artery disease.

Given the grave consequences of atherosclerosis and the costs associated with medical treatments, there is a need for pharmacologic and nutritional interventions that are useful for preventing the occurrence and reoccurrence of these conditions.

Epidemiological studies have noted an inverse correlation between the intake of dietary flavonoids from fruits and vegetables and death from coronary artery disease. This correlation is thought to arise from the antioxidant and platelet inhibition properties of flavonoids found in fruits and vegetables.

Certain flavonoids, including those found in grape seed and grape skin extracts, have been associated with the beneficial health effects observed for aspirin, but without the negative side effects attributed to aspirin. Nevertheless, flavonoid bioavailability or activity is low in many sources of flavonoids. As such, certain dietary sources of flavonoids require large doses to be useful. As a result, many sources of flavonoids are impractical, too costly, or both to be useful on a daily basis.

SUMMARY

The present invention involves the discovery that the combination of certain flavonoids and enzymes in the form of a dietary supplement reduces the dosage of supplement needed to effectively reduce platelet activity and LDL cholesterol oxidation in a mammal. The present invention further involves a method to treat conditions associated with platelet activity and LDL cholesterol oxidation by administering combinations of flavonoids and enzymes to reduce platelet activity and LDL cholesterol oxidation.

In one aspect, the invention features a dietary supplement containing at least one flavonoid source and an enzyme wherein the supplement is effective for inhibiting platelet activity and LDL cholesterol oxidation in a mammal at a dosage of about 30 mg/Kg or less. One example of a dietary supplement in accordance with the invention is PROVEXCV™. It is to be understood that a dosage of supplement as used herein refers to the combined weight of the flavonoid source or sources and enzyme. Further, other ingredients such as fillers, lubricants, carriers and the like may be included as additional ingredients.

The flavonoid source or sources in the dietary supplement may be derived from grape seed extracts, grape skin extracts, ginkgo biloba extracts, bilberry extracts or quercetin. The enzymes may include fungal proteases, acid stable proteases, neutral stable proteases, alkaline stable proteases or bromelain.

In another aspect, the invention features a dietary supplement containing at least one flavonoid source wherein the supplement is effective for inhibiting platelet activity and LDL cholesterol oxidation in a mammal at a dosage of about 30 mg/Kg or less. Preferably, a dietary supplement in accordance with this aspect further includes an enzyme that substantially reduces the dosage required to achieve such inhibition.

In another aspect, the invention features a method to inhibit platelet activity or LDL cholesterol oxidation or both in a mammal by administering a dietary supplement containing a flavonoid source and an enzyme wherein the supplement is effective for reducing platelet activity or LDL cholesterol oxidation at a dosage of about 30 mg/Kg or less. The method may also be used to treat a condition that is associated with platelet activity or LDL cholesterol oxidation by administering a dietary supplement containing a flavonoid source and an enzyme that are effective for reducing platelet activity or LDL cholesterol oxidation.

In another aspect, the invention features an article of manufacture containing a dietary supplement that is effective for reducing platelet activity and LDL cholesterol oxidation contained within a packaging material wherein the packaging material is labeled to indicate that the dietary supplement is effective for reducing platelet activity or LDL cholesterol oxidation or both in a mammal at a dosage of about 30 mg/Kg or less. In another embodiment of the article of manufacture, the packaging material may be labeled to indicate that the dietary supplement is useful to treat a condition that is associated with platelet activity or LDL cholesterol oxidation.

Unless otherwise defined, all technical and scientific terms and abbreviations used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents and other references mentioned herein are incorporated by reference in their entirety. In case of conflict, the present specification, including definitions, will control. Other features and advantages of the invention will be apparent from the following detailed description and from the claims.

DESCRIPTION OF DRAWINGS

FIG. 5 shows a schematic diagram describing the whole blood aggregometry method used herein to measure blood platelet activity ex vivo.

DETAILED DESCRIPTION

The present invention involves the discovery that the combination of certain flavonoids and enzymes in the form of a dietary supplement will reduce the dosage of supplement needed to effectively reduce platelet activity and LDL cholesterol oxidation in a mammal. The present invention further involves a method to treat conditions associated with platelet activity and LDL cholesterol oxidation by administering combinations of flavonoids, extracts and enzymes to reduce platelet activity and LDL cholesterol oxidation.

Coronary artery disease, cerebrovascular disease and peripheral vascular occlusions are characterized by arterial narrowing. If arterial narrowing is further compromised by thrombotic occlusions, blood flow is further decreased and myocardial infarction or stroke may occur. These conditions are associated with platelet activity and LDL cholesterol oxidation. Current treatments for these types of vascular occlusions, such as angioplasty, result in intimal and medial damage to arteries, which can result in restenosis, acute thrombosis, myocardial infarction and sudden coronary death in patients. Moreover, platelet-mediated thrombus formation also plays a role in unstable angina, myocardial infarction and restenosis following angioplasty or atherectomy. The present invention provides a dietary supplement and a method to prevent new and recurrent thrombotic occurrences by administering a dietary supplement that inhibits platelet activity and LDL cholesterol oxidation.

Methods to Evaluate Platelet Activity

1. The Folts Model

The Folts coronary thrombosis model ("Folts model") is used to study platelet aggregation and thrombosis in a variety of animal models. Folts, J. D., *Circulation (Supplement* 4), 83:3–14 (1991); Folts, J. D., *J. Cardiovasc. Drugs & Therapy*, 9:31–43 (1995); Folts et al., *Circulation*, 54:365–370 (1976). The Folts model mimics the problems that occur in patients with narrowed coronary arteries due to atherosclerosis.

To use the Folts model, the chest of a fully anesthetized animal is opened and the heart exposed. Although the experiments described herein involved dogs, other animals amenable to the Folts model include pigs, rabbits, monkeys and other similar animals. Moreover, the Folts model is a model for the clinical syndrome of unstable angina and other platelet-mediated thrombotic events in humans. Samama et al., *Thromb. Haemost.*, 68:500–05 (1992); Raeder et al., *Am. Heart J.*, 104:249–253 (1983); Sherry, S., *Cardiovasc. Rev. Rep.*, 5:1208–19 (1984); Ikeda et al., *J. Am. Coll. Cardiol.*, 21:1008–1017 (1993).

Figure 1:
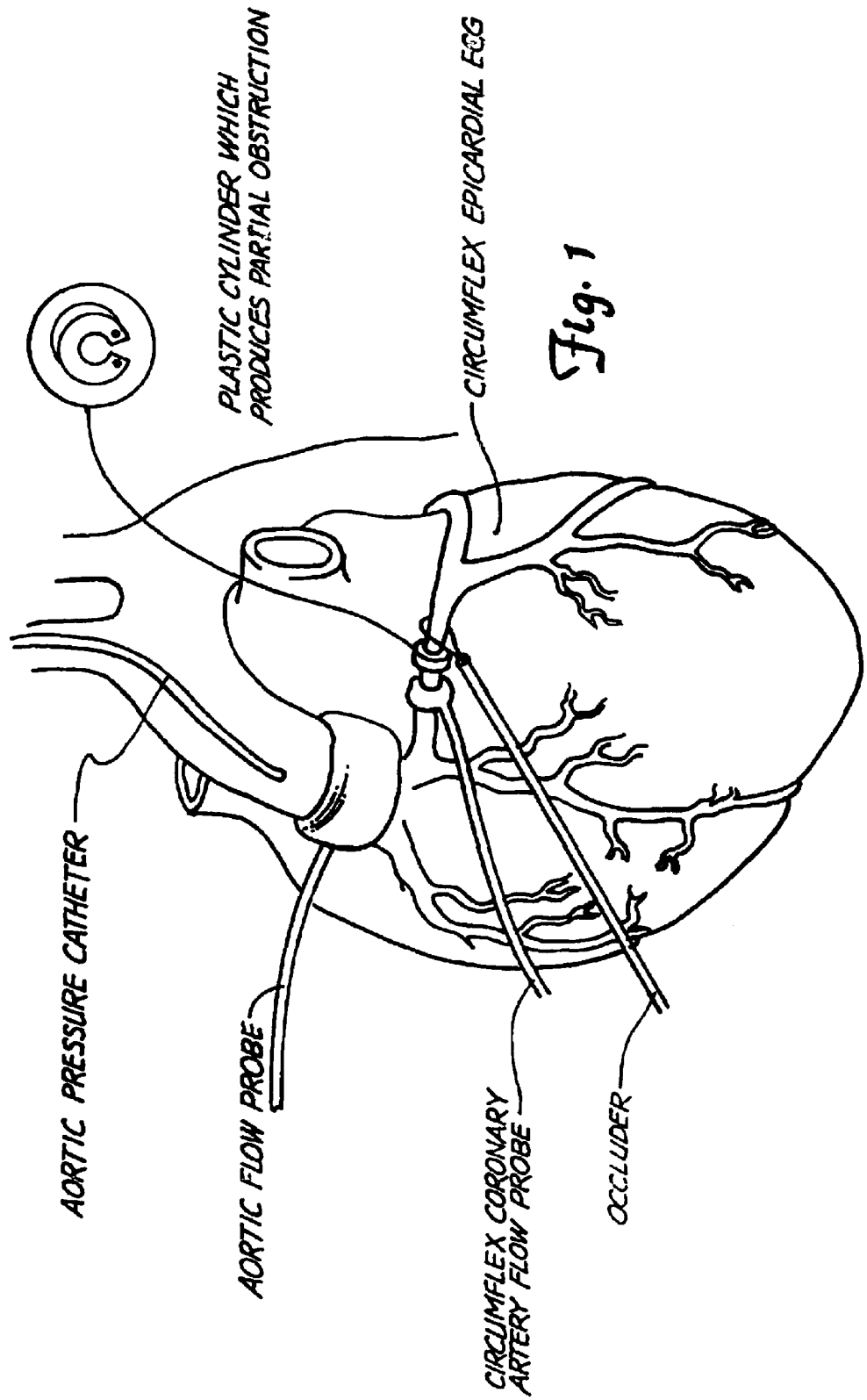
FIG. 1 shows a schematic diagram describing the animal model for producing stenosed arteries to measure changes in coronary blood flow that are observed when periodic thrombosis occurs in order to mimic the problems that occur in patients with narrowed coronary arteries due to atherosclerosis.

As is shown in FIG. 1, the circumflex coronary artery is dissected out and a coronary artery flow probe is placed on the artery. The coronary artery flow probe continuously measures blood flow through the artery without interfering with the artery. The artery is then clamped to create intimal and medial damage to the coronary artery. A plastic constricting cylinder is placed around the outside of the coronary artery at the point of arterial damage to reduce the internal diameter of the coronary artery. The extent of stenosis or diameter reduction produced by the cylinder is altered using an angioplasty balloon or other suitable method.

The coronary artery flow probe measures changes in the coronary artery blood flow when clots periodically develop. When an artery is stenosed, platelets periodically aggregate in the narrowed and damaged part of the coronary artery. Platelet aggregation produces a thrombosis (blood clot) that increases in size, and gradually cuts off the coronary artery blood flow. As the artery becomes occluded, pressure builds up behind the platelet aggregation and may dislodge the clot forcing it through the stenosis, which causes a sudden restoration of coronary blood flow in the narrowed artery. Platelet aggregation in a damaged artery that is sufficient to decrease blood flow is referred to as acute platelet thrombus formation (APTF).

Thrombotic arterial occlusion in human atherosclerotic arteries is thought to begin with the exposure of the thrombogenic surface beneath the intimal lining of an artery. In addition, current information suggests that a variety of different stimuli recruit platelets to adhere and aggregate at an exposed thrombogenic surface. It is to be understood, however, that the scope of the present invention is not limited by a particular theory of pathogenesis.

Figure 2:
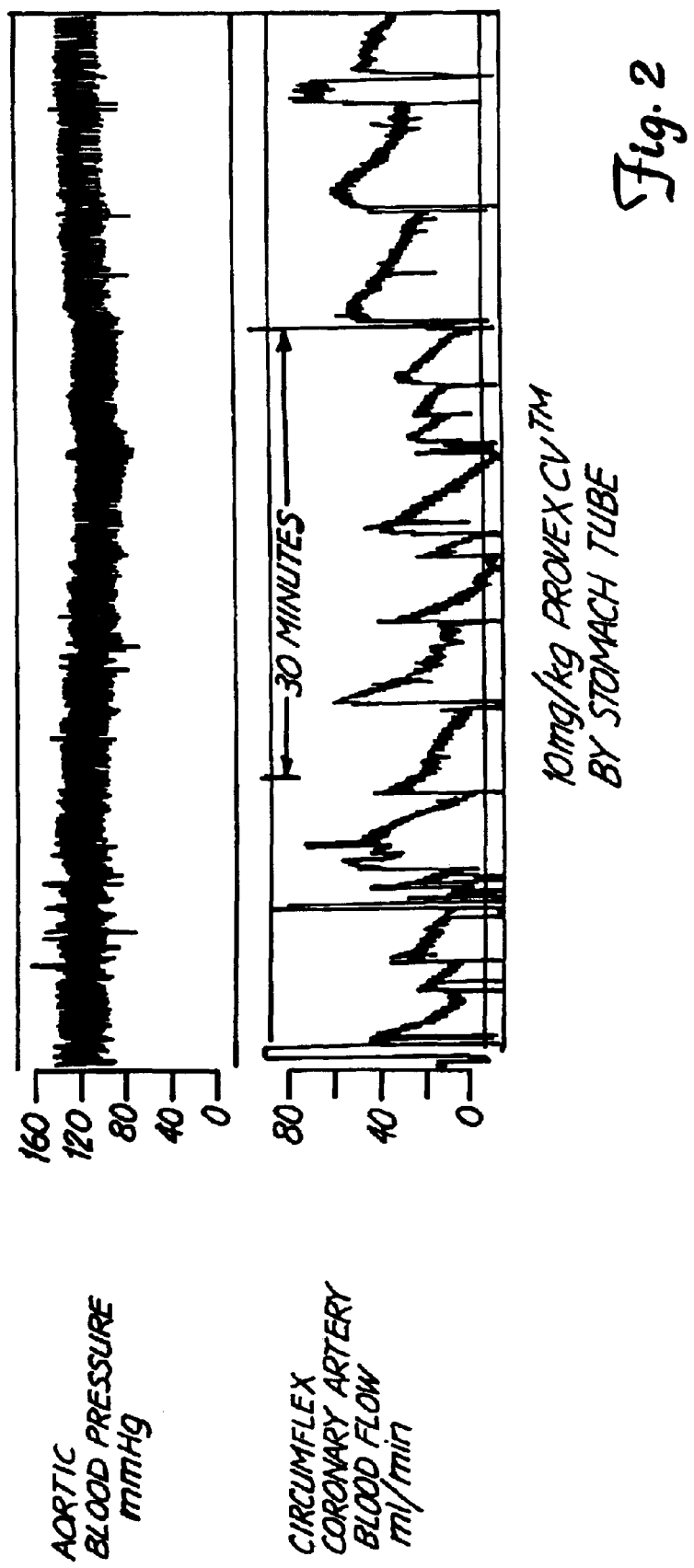
FIG. 2 is a strip chart recording showing the repeated platelet-mediated thrombosis formation followed by embolization, which produces the cyclical flow reductions (CFR's) that are observed for blood flow measured in stenosed arteries produced by the Folts model.

Repeated platelet-mediated thrombosis formation followed by embolization and the observed concomitant changes in blood flow are referred to as cyclical flow reductions (CFR's) or cyclical flow variations (CFV's). This document will use the term CFR's. CFR's have also been observed in damaged and narrowed arteries in humans with femoral artery or coronary artery disease. Folts et al., *Tex. Heart Int. J.*, 9:19–27 (1982); Eichorn et al., *J Am. Coll. Cardiol.*, 17:43–52 (1991). As FIG. 2 shows, CFR's are detected and monitored by measuring coronary artery blood flow. Although FIG. 2 is illustrative of CFR's observed for coronary blood flow, it is to be understood that the Folts method is applicable to arterial flow in general (e.g., femoral arterial flow). In addition, techniques needed to use the Folts model and variations of the model are described in Folts, J. D., *Circulation* (*Supplement* 4), 83:3–14 (1991); Folts, J. D., *J. Cardiovasc. Drugs & Therapy*, 9:31–43 (1995) and the references therein.

The frequency or number of CFR's per unit of time is a direct measure of in vivo platelet activity. Folts, J. D., *J. Cardiovasc. Drugs & Therapy*, 9:31–43 (1995). By measuring the frequency and extent of CFR's in stenosed arteries, the Folts model can be used to evaluate agents that will alter platelet activity. Folts, J. D., *J. Cardiovasc. Drugs Ther.*, 9:31–43 (1995). As such, the Folts model identifies platelet inhibitors, the extent of inhibitor activity, the effective dosages of inhibitors, the duration of inhibition and the ability of an inhibitor to counteract platelet agonists.

Aspirin provides an illustrative example of the Folts model. The Folts model demonstrated that aspirin inhibits platelet activity and eliminates CFR's under the experimental conditions. Folts et al., *Clin. Res.*, 22:595 (1974) (abstract); Folts, J., *Circulation (Supplement 4)*, 83:3–14 (1991); Folts, J. D., *J. Cardiovasc. Drugs Ther.*, 9:31–43 (1995). Aspirin is known to inhibit platelet activity at a dosage of 5 mg/Kg. When platelet activity is inhibited with aspirin under conditions used in the Folts model, platelet activity can be renewed by increasing the concentration of epinephrine (adrenaline) or norepinephrine in the blood. This increase in adrenaline occurs naturally in many people when they are stressed, scared, anxious or exercising. Folts, J. D. & Rowe, G. G., *Thromb. Res.*, 50:507–516 (1988). In addition, increasing the arterial stenosis will also cause a recurrence of CFR's abolished with aspirin. Folts, J., *Circulation (Supplement 4)*, 83:3–14 (1991). As such, the Folts model provides an effective tool to evaluate inhibition of platelet activity.

2. The Platelet Aggregometry Test

A second method to measure platelet activity in humans or animals is the whole blood platelet aggregometry test. Equipment and methods to perform whole blood platelet aggregometry evaluations described and used herein are available from Chronolog Inc., 2 West Park Rd., Haverton, Pa. 19083. To perform the test, a blood sample is drawn by standard methods, which is then placed in a plastic tube. A pair of electrodes is placed in the blood sample to measure the electrical resistance of the blood sample. The electrical resistance of blood is normally low due to the numerous ions and electrolytes found in blood. A known platelet aggregation stimulus, such as adenosine diphosphate (ADP) or collagen, is then added to the blood sample to activate the platelets. Activated platelets will adhere to the electrodes used in a platelet aggregometry test. As shown in FIG. 5 (right side), the electrical resistance of the blood sample usually increases in a sigmoidal fashion as platelets aggregate on the electrodes. If a subject is administered a substance that inhibits platelet activity, the increase in resistance following the addition of a platelet stimulus will be smaller.

Aspirin provides an illustrative example of the use of the blood aggregometry test. A blood sample taken from a human will have a baseline level of platelet activity. Addition of ADP increases the resistance of the blood sample. See FIG. 5, right side, "ADP" curve. A second blood sample is withdrawn two hours after the person is given a 325 mg tablet of aspirin. Platelet activation following the addition of ADP does not increase platelet activity to the level observed for the initial blood sample. See FIG. 5, right side, "ADP+ASA" curve. The decrease in blood resistance observed is expressed as a percentage decrease in ex vivo platelet activity caused by aspirin. When epinephrine levels of a person, who has ingested aspirin, are raised prior to withdrawing a blood sample, the inhibitory effects observed for aspirin are diminished. See FIG. 5, right side, "ADP+ASA+EPI" curve. Folts, J. D., *J. Cardiovascular Drugs & Therapy*, 9:31–43 (1995); Ingerman-Wojenski & Silver, *Thromb. Haemost.*, 51:154–156 (1984).

Aspirin also responds similarly when collagen is used to stimulate platelet activity. When collagen is used to stimulate platelet activity in the blood aggregometry test, aspirin decreases platelet activity by about 30–40%. Therefore, the blood aggregometry technique may also be used as another measure of platelet inhibitory effectiveness produced by drugs or flavonoids.

3. Evaluating LDL Cholesterol Oxidation

LDL cholesterol oxidation or protection therefrom can be determined by several methods. Kleinveld et al., *Clin. Chem.*, 38(10):2066–2072 (1992) describes the methods for the LDL oxidation experiments described and used herein. A preferred way to practice the method encompasses extracting LDL cholesterol from whole blood samples collected from a subject using standard techniques. The extracted LDL cholesterol is divided into control and experimental samples. LDL oxidation is catalyzed by adding a copper ion solution to each LDL cholesterol sample. Copper ions are known to catalyze and enhance LDL cholesterol oxidation.

Control LDL cholesterol samples contain extracted LDL cholesterol and copper ions. The control samples provide a baseline measure of the antioxidants in the diet of the subject from whom the blood was drawn and in the LDL cholesterol prepared therefrom. Test LDL cholesterol samples are combined with copper ions in the presence or absence of additional compounds such as dietary supplements that may act as antioxidants.

Additionally, a subject may be administered an antioxidant by standard techniques prior to collecting a blood sample, which facilitates the measurement of antioxidant properties in vivo. To measure in vivo LDL cholesterol antioxidant properties, whole blood samples are obtained before and after administering an antioxidant source to be tested.

Figure 6:
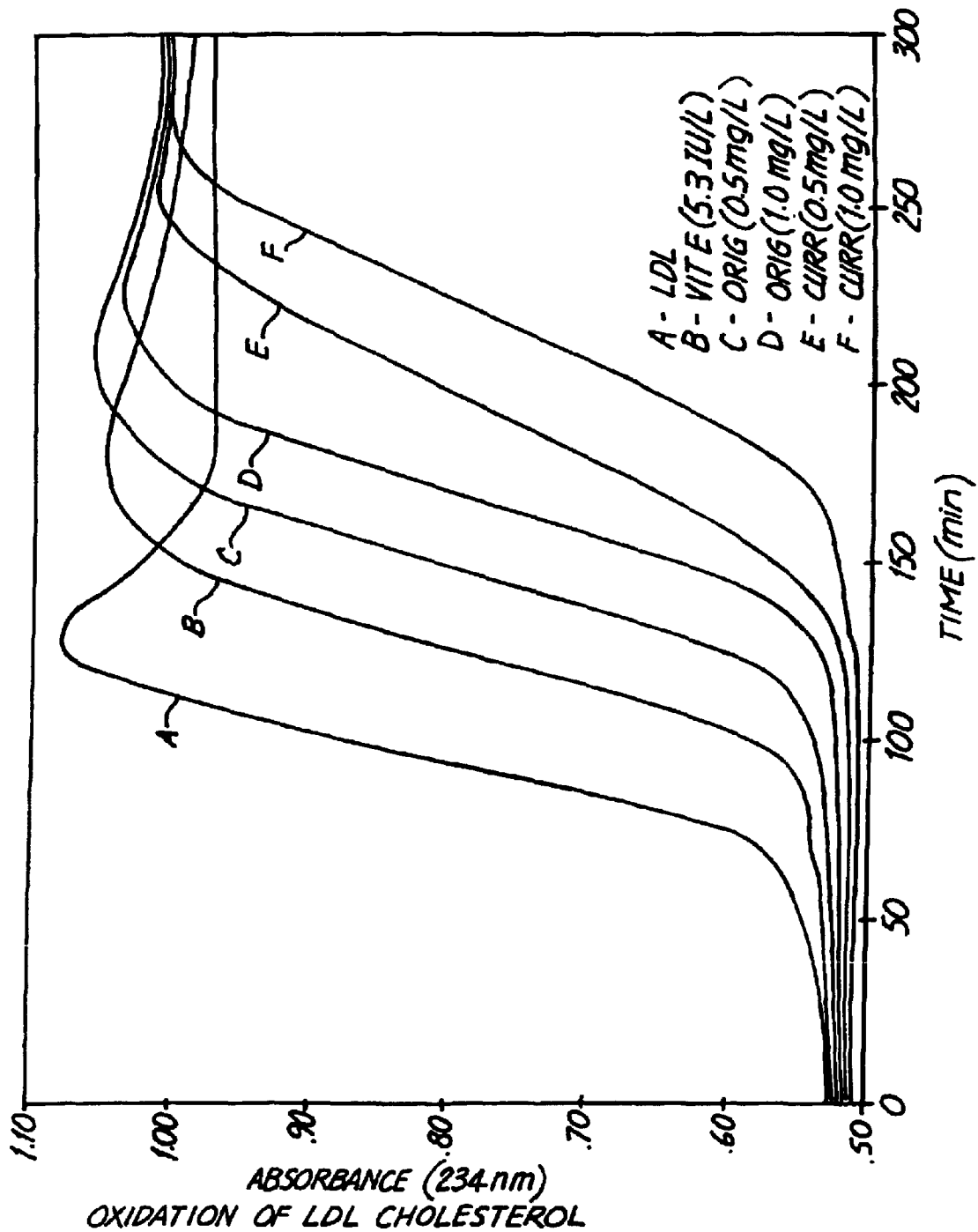
FIG. 6 is a graph showing the time course of LDL cholesterol oxidation monitored at 234 nm in the presence of vitamin E, ProVex Plus™ or PROVEXCV™.

Copper ions accelerate the production of conjugated dienes in LDL cholesterol oxidation, which absorb light at 234 nm. Therefore, LDL cholesterol oxidation is monitored by following the increase in absorbance at 234 nm as a function of time as shown in FIG. 6. Antioxidants prolong the onset of diene production in LDL cholesterol. As a result, LDL cholesterol samples containing antioxidants can be compared by computing the time elapsed before LDL cholesterol oxidation is observed (lag time). See FIG. 7. The lag time is the best indicator of the LDL cholesterol protection from oxidative damage under the LDL oxidation experimental conditions described herein. Longer lag times denote better antioxidant properties.

Inhibiting Platelet Activity and Decreasing LDL Cholesterol Oxidation

Many complex factors lead to atherosclerosis, coronary artery disease and related conditions. Among these factors, it is known that platelet interaction with arterial walls can enhance the atherosclerotic process. Furthermore, increased platelet activity is intimately involved in both the development of atherosclerosis and the transient and permanent occurrence of thrombotic events. Therefore, factors that reduce platelet activity on a daily basis should inhibit the development or occurrence of atherosclerosis, coronary artery disease and related conditions. Folts et al., *J. Myocard. Ischemia*, 6(8):33–40 (1994).

Epidemiological studies reveal a inverse correlation between the consumption of foods high in antioxidant flavonoids or vitamin E with reduced coronary heart disease. Hertog et al., Lancet, 342(8878):1007–11 (1993); Waterhouse et al., *Hypernutritious Foods*, Agscience, Inc., Auburndale, Fla., 219–238 (1997). Food sources known to contain flavonoids include red wine, beer, grape juice, fruits and vegetables. Extracts from grape seeds, grape skins, ginkgo biloba, bilberry and other similar fruits, vegetables and herbs are also flavonoid and antioxidant sources.

There are, however, hurdles that must be overcome to effectively obtain the benefits that are associated with flavonoids and antioxidants. One hurdle is the bioavailability of the active ingredients in dietary sources of flavonoids. When bioavailability or activity is low, a person must consume large quantities of a platelet inhibitor or antioxidant dietary supplement to receive the benefits associated with a platelet inhibitor or antioxidant. As a result, low bioavailability may render a dietary supplement impractical, too costly or both for many consumers.

In addition, the effectiveness of the platelet inhibition and antioxidant characteristics associated with individual flavonoids varies between particular flavonoids, e.g., flavonoids from grapes are better platelet inhibitors in human volunteers and animals than flavonoids found in citrus fruit juices. Folts et al., *J. Am. Coll. Cardiology,* 29(2) (Supplement A):303A (1997); Folts, J. D., *J. Am. Coll. Cardiology,* 29(2)(Supplement A):226A (1997); Folts et al., *J. Am. Coll. Cardiology,* 29(2)(Supplement A):180A (1997).

Moreover, the environmental conditions within the blood stream are not static. To be effective, a dietary supplement must be effective under a variety of conditions including various degrees of stress, excitement and exercise, which tend to elevate platelet activity levels.

Finally, many dietary sources of flavonoids also contain unwanted constituents such as the alcohol in wines and beers and the sugars and calories in grape juice. There are also toxicity concerns for various flavonoids and drugs. For example, aspirin has well documented side effects that include gastrointestinal irritation, loss of effectiveness in the presence of epinephrine and the inability to inhibit CFR's under extreme stenosis circumstances.

Therefore, it was hypothesized that it would be useful to create a dietary supplement that would inhibit platelet activity and LDL cholesterol oxidation under a variety of conditions in a practical and cost effective manner. It was further hypothesized that a key feature of a useful dietary supplement would be to increase the bioavailability of a dietary supplement by including constituents to enhance the absorption of the dietary supplement active ingredients. The present inventor has discovered such a supplement and the supplement is described and claimed herein.

In a first embodiment, the invention provides a dietary supplement containing at least one flavonoid source and an enzyme that are effective for inhibiting blood platelet activity and LDL cholesterol oxidation in a mammal at a dosage of about 30 mg/Kg or less. The dietary supplement may further contain flavonoid sources such as grape seed extracts, grape skin extracts, ginkgo biloba extracts, quercetin, bilberry extracts or any other specific flavonoid. The "flavonoid source" may be derived from any source and may include synthetic or purified flavonoids from known sources. The flavonoid source may also be, for example, one or more flavonoids determined to be highly active alone or as a combination wherein the flavonoid is isolated from a complex mixture, such as a plant extract, containing numerous flavonoids.

While not bound by a particular theory of action, it is believed that the constituents of the presently disclosed dietary supplement act synergistically by increasing bioavailability or pharmacologic interactions, to inhibit blood platelet activity and inhibit LDL cholesterol oxidation. In a related aspect of the invention, the dietary supplement remains effective for reducing platelet activity and inhibiting LDL cholesterol oxidation in the presence of elevated platelet agonist (e.g., epinephrine) concentrations.

Examples of dietary supplement formulations may include one or more of the following constituents: fruit extracts, vegetable extracts, digestive enzymes, herbs, flavonoids, antioxidants and other similar items.

Illustrative examples of useful digestive enzymes include pepsin, papain, fungal proteases, acid stable proteases, neutral stable proteases, alkaline stable proteases and bromelain.

Illustrative examples of useful flavonoids include catechins, procyanidins, proanthocyanidins, quercetin, rutin and glycosidic forms of the flavonoids.

Dietary supplements of the present invention may be delivered orally, intravenously, subcutaneously, sublingually, intragastricly, as a phytosome or by any acceptable delivery method. In addition, the dietary supplement may be combined with any suitable carrier to facilitate delivery. Dietary supplements tested herein using the Folts model were administered either intravenously or intragastricly. Absorption through the stomach lining usually takes 2–4 hours. As such, dietary supplements administered intragastricly may not affect CFR's until about 2–4 hours after administering a dietary supplement.

Commercial dietary supplements are generally formulated to be given orally. Useful forms of administration for dietary supplements include pills, pastes, powders, liquids and other common oral formulations. Preparations of the dietary supplements may be manufactured using common manufacturing techniques for the various forms of the supplement described herein. The dietary supplements described herein additionally may contain magnesium stearate as a lubricant to facilitate the delivery the supplement into capsules. Magnesium stearate is generally used at concentrations from 1–4 mg/capsule, preferably 1–2 mg/capsule.

The Folts model may be used to identify dietary supplement formulations that decrease platelet activity. A dog coronary artery is prepared to exhibit CFR's as described herein. The dog is then administered measured doses of a dietary supplement by one of the approved methods. The effect that the dietary supplement dose has on the observed CFR's is monitored. By using the Folts model, the effective dose, half life and extent of absorption can be determined. Blood samples taken from the dog provide information concerning supplement concentrations and platelet activity levels within the blood stream.

Additional experiments may be used to evaluate the characteristics of useful dietary supplements. For example, the stenosis severity can be increased following administering a dietary supplement to determine if CFR's reoccur. In addition, platelet agonists administered at various time points preceding or following administering a dietary supplement will identify dietary supplements that can sustain CFR elimination under platelet activating conditions. Useful agonists include epinephrine and norepinephrine. Useful doses of epinephrine for this purpose include epinephrine administered intravenously at 0.2 $\mu$g/Kg/min for 15 minutes.

Human volunteers or patients with human coronary artery disease may also be administered the dietary supplements described and claimed herein and variations thereof to evaluate the efficacy of the dietary supplement using platelet aggregometry and LDL cholesterol oxidation experiments as described herein.

Useful dietary supplement formulations may include one or more of the following: grape seed extract, grape skin extract, ginkgo biloba extract, bilberry extract, quercetin and an enzyme blend. The dietary supplement may be formulated by weight in the following manner: grape seed extract at 12% w/w, grape skin extract at 20% w/w, ginkgo biloba extract at 10% w/w, bilberry extract at 10% w/w, quercetin at 24% w/w and an enzyme blend at 24% w/w.

As such, a useful dietary supplement containing flavonoids and enzymes in accordance with the present invention is PROVEXCV™. PROVEXCV™ is available from Melaleuca, Inc., Idaho Falls, Id.

PROVEXCV™ contains the following ingredients per 380 milligram capsule:

| Ingredient | % Formulation | Amount |
|---|---|---|
| Grape Seed Extract | 12% | 45 mg |
| Ginkgo Biloba Extract | 10% | 38 mg |
| Bilberry Extract | 10% | 38 mg |
| Grape Skin Extract | 20% | 76 mg |
| Quercetin | 24% | 92 mg |
| Enzyme Blend | 24% | 91 mg |
| Total | 100% | 380 mg |

A supplement may also be prepared, in accordance with the present invention, to include all of the above ingredients except the Enzyme Blend.

The enzyme blend used in each 380 milligram capsule of PROVEXCV™ contains the following enzymes:

| Ingredient | % of Enzyme blend | Activity Units | |
|---|---|---|---|
| Fungal Protease 20053 | 25% | 11,250 | HUT |
| Fungal Protease 20054 | 25% | 11,250 | HUT |
| Acid Stable Protease | 25% | 3,375 | SAPU |
| Bromelain | 25% | 5,760,000 | PU |
| Total | 100% | | |

The fungal proteases 20053 and 20054 are enzyme mixtures of acid, neutral and alkaline protease enzymes. HUT activity is the activity of an enzyme measured in the FCC HUT assay, which is based on the hydrolysis of denatured hemoglobin. One HUT unit is defined as that amount of enzyme that produces a hydrosylate whose absorbance at 275 nm is equal to a solution of 1.10 mg/ml of tyrosine in 0.006 N HCl in one minute. SAPU activity is measured in the FCC SAPU assay, which is based on hydrolysis of Hammarstan casein substrate. One SAPU unit is defined as that amount of enzyme that will liberate one $\mu$mole of tyrosine per minute at pH 3 and 37° C. PU activity is the activity of an enzyme measure in the FCC PU assay, which is based on the hydrolysis of casein. One PU unit is defined as the amount of enzyme that liberates 1 $\mu$g of tyrosine per hour at pH 6.0 and 40° C. More information concerning the above referenced enzymes is available from the National Enzyme Company, Forsyth, Mo., (417)-546-4796 through technical bulletins concerning the enzymes.

The ingredients contained in PROVEXCV™ can be obtained from the following sources. The actual sources used are indicated by underlining the supplier.

| Ingredient/Extract | Available from |
|---|---|
| Grape Seed Extract | Indena - Milan, Italy |
| | Polyphenolics - Canandaigua, NY |
| | InterHealth - Concord, CA |
| | Tri-K Industries-Fanerson, NJ |
| Ginkgo Biloba Extract | Indena - Milan, Italy |
| | Weinstein Nutritional - Irvine, CA |
| | OptiPure - Los Angles, CA |
| | Botanicals International - Long Beach, CA |
| Bilberry Extract | Indena - Milan, Italy |
| | OptiPure - Los Angeles, CA |
| | Chemco Industries - Los Angeles, CA |
| Grape Skin Extract | Freeman Industries - Tuckahoe. NY |
| | Weinstein Nutritional - Irvine, CA |
| | Brucia Extracts - California |
| Quercetin | Weinstein Nutritional - Irvine, CA |
| | Botanicals International - Long Beach, CA |
| | Triarco Industries - Wayne, NY |
| Enzyme Blend | National Enzyme Co. - Forsyth. MO |
| | MakWood - Thiensville, WI |
| | Botanicals International - Long Beach, CA |
| Citrus Extract | Botanicals International - Long Beach. CA |

ProVex Plus™ contains the following ingredients per 125 milligram capsule:

| Ingredient | % Formulation | Amount |
|---|---|---|
| Grape Seed Extract | 20% | 25 mg |
| Ginkgo Biloba Extract | 8% | 10 mg |
| Bilberry Extract | 8% | 10 mg |
| Grape Skin Extract | 24% | 30 mg |
| Citrus Extract | 40% | 50 mg |
| Total | 100% | 125 mg |

Experiments in the Folts model using a supplement containing all of the ingredients of PROVEXCV™ except the enzyme blend have shown that such a supplement is effective for eliminating CFR's at a dosage of about 20 mg/Kg or less. It has been discovered that the dosage needed to eliminate CFR's observed in the Folts model can be further reduced by combining a dietary flavonoid with an enzyme. The addition of an enzyme blend containing equal parts of two fungal proteases, an acid stable protease and bromelain to a supplement containing all of the ingredients of PROVEXCV™ except the enzyme blend decreased the dosage needed to eliminate CFR's in the animal model used herein from about 20 mg/Kg to about 10 mg/Kg.

The effectiveness of PROVEXCV™ was such that the PROVEXCV™ decreased the dosage needed to eliminate CFR's in the animal model used herein from about 30 mg/Kg needed for ProVex Plus™ to about 10 mg/Kg for PROVEXCV™. As a result, useful doses of dietary supplements described herein are about 30 mg/Kg or less. Preferably, an effective dosage is about 20 mg/Kg or less. More preferably, an effective dosage is about 10 mg/Kg or less.

As such, the consumption of PROVEXCV™ with its antioxidant and platelet inhibitory properties may protect against the development of coronary artery disease, acute occlusive thrombosis, death from myocardial infarction and other conditions that are associated with platelet activity and LDL cholesterol oxidation.

Another embodiment of the invention includes a dietary supplement designated PROVEXCV2™. Like ProVex Plus™ and PROVEXCV™, PROVEXCV2™ can be used as a dietary supplement to inhibit platelet activity or LDL cholesterol oxidation. PROVEXCV2™ contains the following ingredients per 1,638 milligrams:

| Ingredient | % Formulation | Amount |
|---|---|---|
| Enzyme Blend | 4.58% | 75 mg |
| Grape Seed Extract | 3.30% | 54 mg |
| Grape Skin Extract | 67.77% | 1,110 mg |
| Quercetin | 7.32% | 120 mg |
| Ginkgo Biloba Extract | 9.71% | 159 mg |
| Bilberry Extract | 7.32% | 120 mg |
| Total | 100% | 1,638 mg |

The ingredients for the dietary supplements described herein, including PROVEXCV2™, can be obtained from any supplier. For example, the suppliers listed above can be used to obtain all the ingredient for PROVEXCV2™. In addition, the ingredients can be obtained from sources that were not subjected to a fermentation process. For example, unfermented grape seed extract and unfermented grape skin extract can be used as ingredients for the dietary supplements described herein. Such unfermented ingredients can be obtained from any supplier such as Polyphenolics (Canandaigua, N.Y.).

Briefly, fermentation processes are used during the production of wine. If an ingredient is obtained from a supplier involved in wine production, then the ingredient could be a fermented ingredient. For example, a fermented ingredient, such as fermented grape seed extract or fermented grape skin extract, can be any ingredient isolated from a source, such as grapes, that were subjected to fermentation. In contrast, an unfermented ingredient can be any ingredient isolated from a source not subjected to fermentation. Such unfermented ingredients can be more effective sources of flavonoids than fermented ingredients. For example, unfermented grape seed extract or unfermented grape skin extract can inhibit platelet activity or LDL cholesterol oxidation more effectively than fermented grape seed extract or fermented grape skin extract.

It is noted that the percentage for each ingredient in ProVex Plus™, PROVEXCV™, and PROVEXCV2™ can be changed, provided the resulting composition can inhibit platelet activity or LDL cholesterol oxidation. For example, the percentage of ginkgo biloba extract can be increased to greater than 10%.

In another aspect, the invention provides a method to inhibit platelet activity or LDL cholesterol oxidation in a mammal by administering a dietary supplement containing at least one flavonoid source and an enzyme that are effective for reducing platelet activity or LDL cholesterol oxidation or both.

In another aspect of the invention, a method to treat a condition associated with platelet activity or LDL cholesterol oxidation in a mammal is provided. The method involves the step of administering a dietary supplement containing at least one flavonoid source and an enzyme that are effective for reducing platelet activity or LDL cholesterol oxidation at a dosage of about 30 mg/Kg or less.

To practice the described methods, a mammal is given a dose of a dietary supplement as described herein by an acceptable delivery method. The dose can be administered hourly, daily, weekly or a fraction thereof depending on the circumstances. After administration of the dietary supplement a mammal can be evaluated for platelet activity and LDL cholesterol oxidation. The platelet activity and LDL cholesterol oxidation levels can then be compared to the same levels prior to administering the dietary supplement.

In another aspect of the invention, an article of manufacture containing a dietary supplement that is effective for reducing platelet activity and LDL cholesterol oxidation is provided. The article is contained within a packaging material that is labeled to indicate that the dietary supplement is useful for reducing platelet activity or LDL cholesterol oxidation or both in a mammal at a dosage of about 30 mg/Kg or less. In another embodiment of the article of manufacture, the packaging material can be labeled to indicate that the dietary supplement is useful to treat a condition that is associated with platelet activity or LDL cholesterol oxidation.

Any common packaging and printing method can be used to prepare the article of manufacture.

The invention will be further understood with reference to the following illustrative embodiments, which are purely exemplary, and should not be taken as limiting the true scope of the present invention as described in the claims.

EXAMPLES

Example 1

Evaluating Platelet Inhibition by Dietary Supplements

Figure 3:
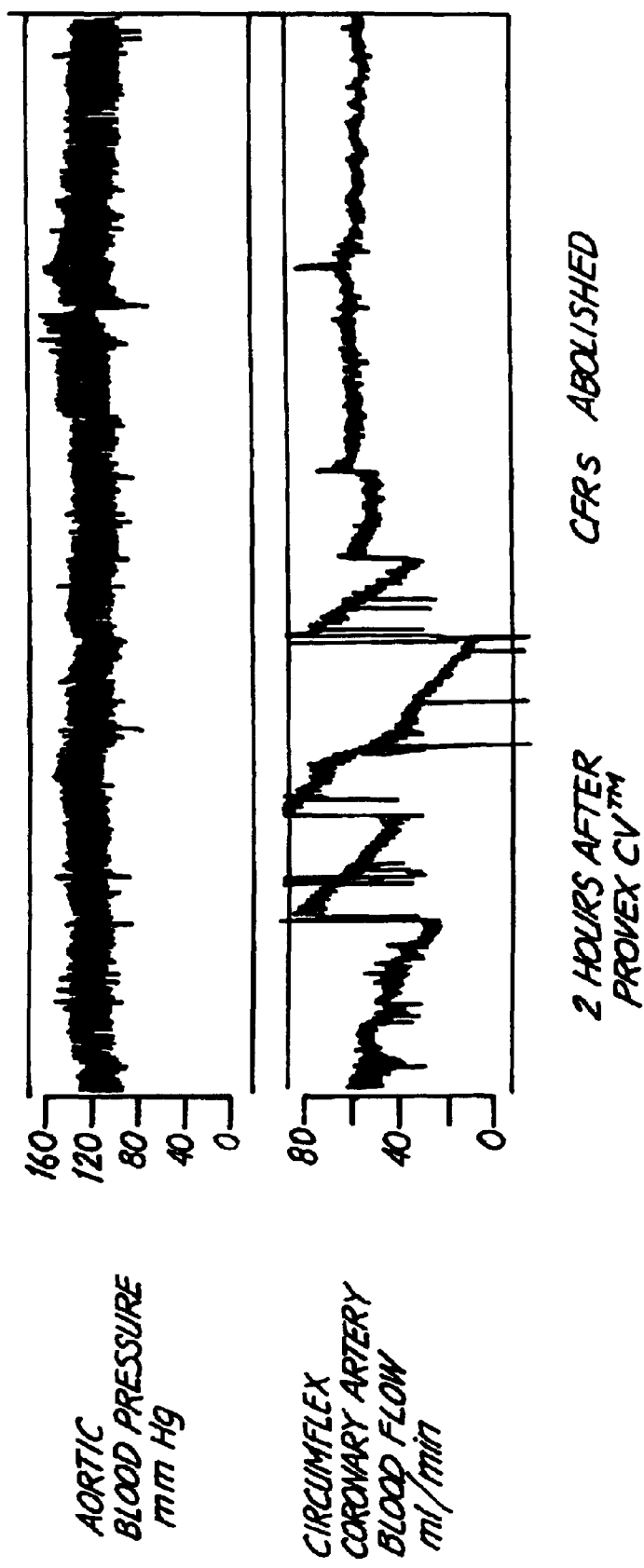
FIG. 3 is a strip chart recording showing the elimination of CFR's following ingestion of PROVEXCV™ due to the in vivo platelet inhibiting properties of PROVEXCV™, which is a preferred dietary supplement in accordance with the invention.

Ten anesthetized dogs with coronary stenosis and medial damage were prepared for evaluation using the methods of the Folts model as disclosed in Folts, J., *Circulation* (*Supplement* 4), 83:3–14 (1991). Blood pressure and coronary artery blood flow were monitored continuously throughout the experiment. As exemplified in FIG. 2, CFR's similar to the CFR's shown in FIG. 2, which were due to acute platelet thrombus formation (APTF), occurred 8±3 times in a 30 min interval in 10 dogs prior to administering PROVEXCV™. All figures showing strip chart recordings are on the same scale, which is 10 minutes per twelve squares. 10 mg/Kg of PROVEXCV™ was then administered by stomach tube to each dog. As exemplified in FIG. 3, gastric administration of 10 mg/Kg of PROVEXCV™ eliminated the observed CFR's in 174±24 min in 9 of the 10 dogs. The CFR's observed in the tenth dog were reduced to 2 CFR's in a 30 minute interval three hours after administering 10 mg/Kg PROVEXCV™. There was no change in heart rate or arterial blood pressure produced by the dietary flavonoids in PROVEXCV™.

Figure 4:
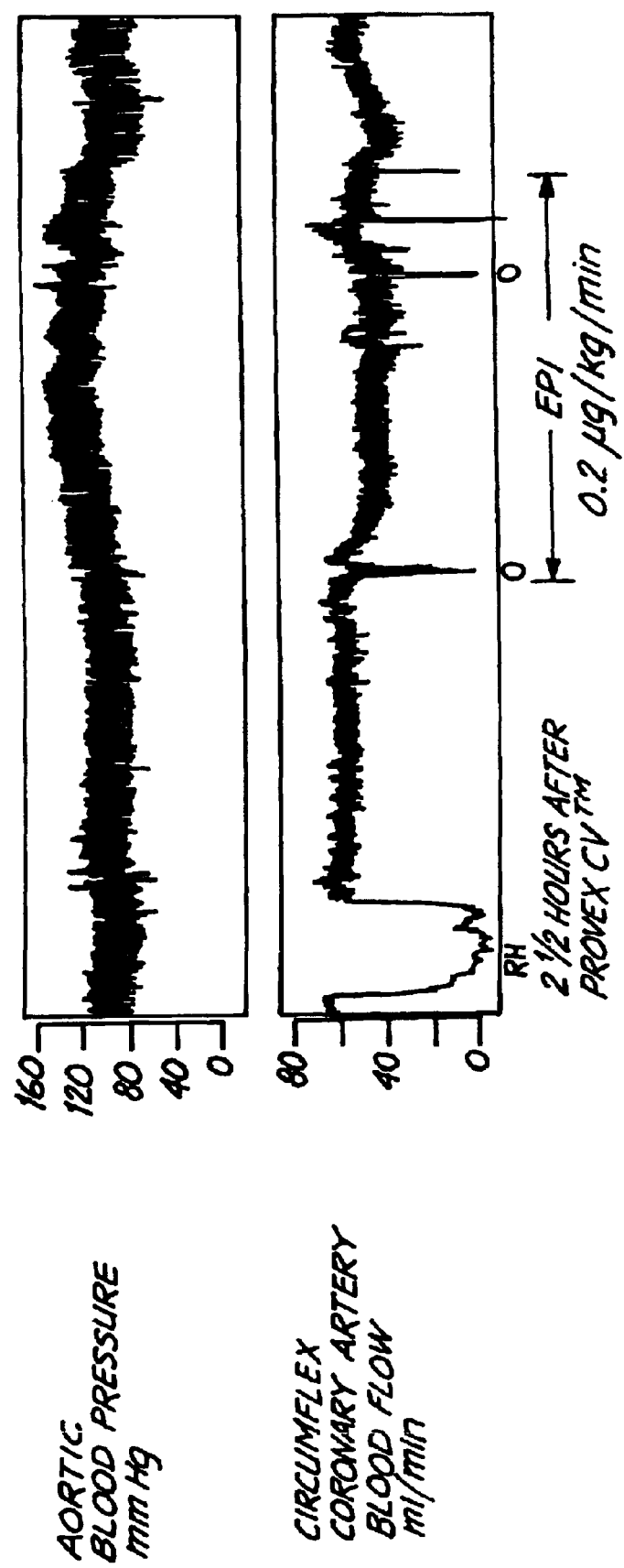
FIG. 4 is a strip chart recording showing that the CFR's eliminated by administering PROVEXCV™ did not reappear when epinephrine (adrenaline) was administered two and one half hours after administering PROVEXCV™.

When evaluated in the Folts model, platelet activity that is inhibited by aspirin can be reactivated by administering 0.2 μg/Kg/min epinephrine intravenously. Folts, J., *Circulation* (*Supplement* 4), 83:3–14 (1991). Eight dogs that had CFR's eliminated by administering 10 mg/Kg PROVEXCV™ were administered 0.2 μg/Kg/min epinephrine intravenously for 15 minutes. The right side of FIG. 4 shows that CFR's eliminated by gastric administration of 10 mg/Kg PROVEXCV™ did not reappear when epinephrine was administered at 0.2 μg/Kg/min intravenously for 15 minutes in all 8 dogs.

Ex vivo platelet activity was determined for all ten dogs using the whole blood aggregometry method as described herein. Blood samples were taken from each dog before and after the administration of 10 mg/Kg of PROVEXCV™ and tested. When platelet aggregation was stimulated by collagen, ex vivo whole blood platelet aggregation was decreased by 40%±9% in all 10 dogs administered 10 mg/Kg PROVEXCV™. Unlike aspirin as shown in FIG. 5, the observed platelet aggregation increases in response to epinephrine were not observed with PROVEXCV™.

Example 2

Evaluating LDL Cholesterol Oxidation of Dietary Supplements

As described above, LDL cholesterol oxidation is commonly measured by observing absorbance at 234 nm ($AbS_{234nm}$) as a function of time while the LDL cholesterol is exposed to oxidative conditions. The antioxidant effectiveness of PROVEXCV™ and other substances was determined.

LDL cholesterol was prepared from human volunteer blood samples. Isolated LDL cholesterol was then mixed with a buffer, vitamin E, ProVex Plus™ ("Orig" in FIG. 6) or PROVEXCV™ ("Curr" in FIG. 6). Experimental solutions of ProVex Plus™ and PROVEXCV™ were prepared at 0.5 and 1.0 mg/L final concentration. The concentrations chosen for ProVex Plus™ and PROVEXCV™ were an estimate of expected blood levels of the dietary supplements based on accepted blood absorption models. To each sample a measured amount of copper ions was added. The amount of vitamin E used was comparable to the amount anticipated to be in the blood of a person administered 400 IU of vitamin E.

After mixing, the $AbS_{234nm}$ of each solution was then monitored as a function of time. As shown in FIG. 6, incubating LDL cholesterol with ProVex Plus™ or PROVEXCV™ at 0.5 mg/L or 1.0 mg/L protected LDL cholesterol from oxidation longer than that observed for a well known antioxidant vitamin E at 5.3 IU/L.

Figure 7:
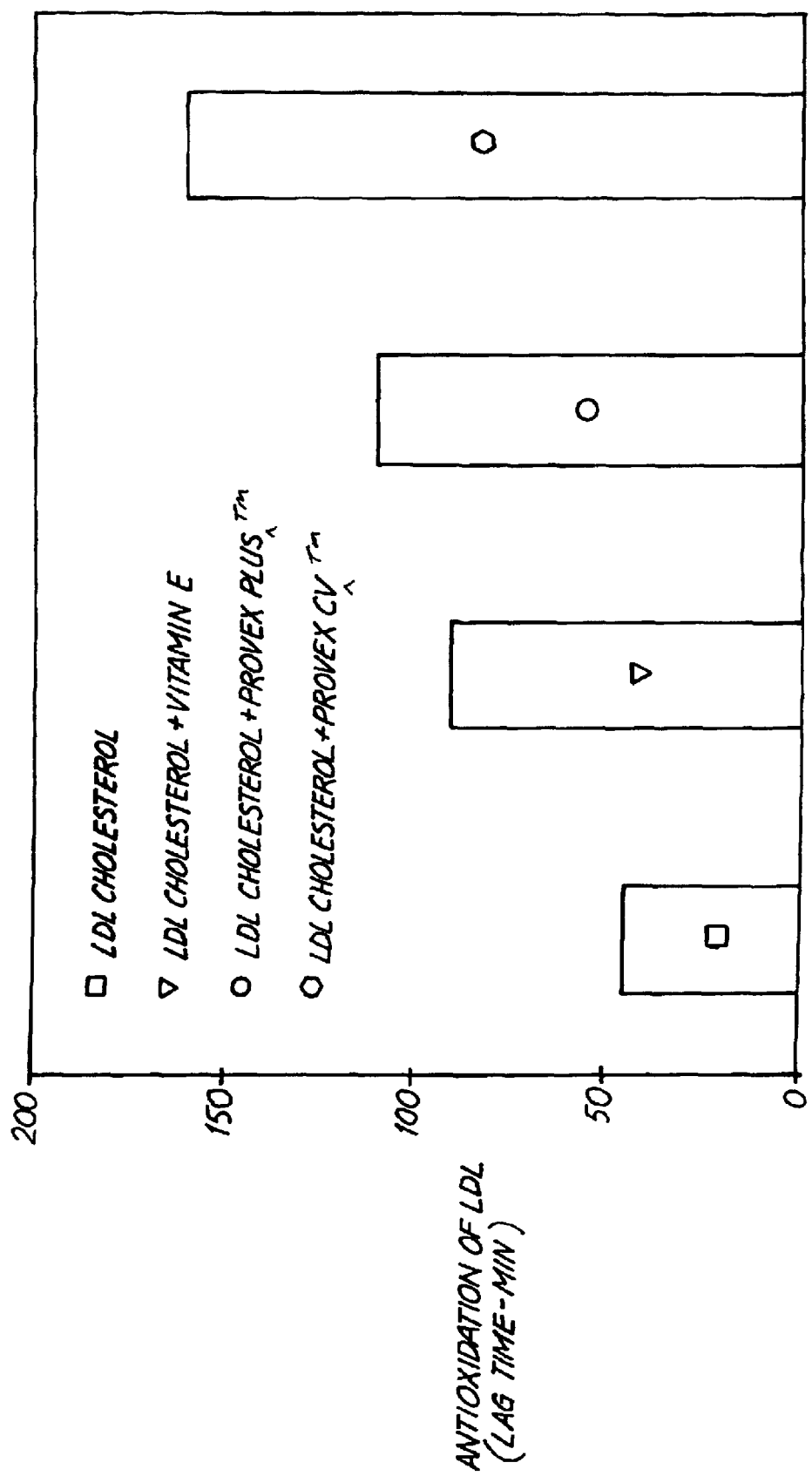
FIG. 7 shows a graph of the level of protection against LDL cholesterol oxidation provided by PROVEXCV™.

As shown in FIG. 7, LDL cholesterol did not demonstrate appreciable oxidation until 45 minutes following the addition of copper ions. Vitamin E at the described concentration protected LDL cholesterol from oxidation for about 95 minutes. 1.0 mg/L of ProVex Plus™ protected LDL cholesterol against oxidation for more than 100 minutes. Finally, 1.0 mg/L of PROVEXCV™ protected LDL cholesterol against oxidation for more than 150 minutes under these experimental conditions. As such, ProVex Plus™ and PROVEXCV™ are better antioxidants than vitamin E.

Example 3

Evaluating PROVEXCV2™

In dogs, the effects of PROVEXCV2™ on platelet activity was evaluated in vivo using the Folts model and ex vivo using the whole blood platelet aggregometry test. Briefly, ten adult mongrel dogs of either sex were anesthetized and the chest opened at the fifth intercostal space. The left circumflex coronary artery was dissected out and an electromagnetic flow probe placed around the artery to measure coronary blood flow. Distal to the flow probe, the artery was clamped three times with a special surgical clamp to produce intimal and medical damage. A plastic cylinder of appropriate inside diameter was placed around the artery to produce a 70% reduction in arterial diameter.

During the occurrence of CFR's, a blood sample was drawn for the ex vivo the whole blood platelet aggregometry test. After monitoring consistent formation of CFR's for 20 minutes, 15 mg/kg of PROVEXCV2™ was administered by a stomach tube. The CFR's were monitored for 3 hours. When the CFR's were abolished, a second blood sample was drawn to repeat the ex vivo platelet aggregation test. Epinephrine (0.2 µg/kg/min) was then infused for 20 minutes to observe whether the CFR's could be renewed.

The ten dogs with coronary artery stenosis and intimal damage had CFR'S, due to acute platelet thrombus formation, at a frequency of 7±3 per 30 minutes. After 15 mg/kg of PROVEXCV2™ was given by gastric tube, the CFR's were abolished for 164±29 minutes. The intravenous infusion of epinephrine (0.2 µg/kg/min for 20 minutes) did not renew the CFR's in any dog. Again, epinephrine infusion after the abolishment of CFR's with 5–10 mg/kg of aspirin can result in renewed CFR's in 50–60% of dogs studied. Thus, PROVEXCV2™ appears to inhibit platelet activity more potently than aspirin.

The activity of platelets in whole blood samples collected before and after PROVEXCV2™ administration were evaluated ex vivo using the whole blood platelet aggregometry test. After PROVEXCV2™ administration, platelet aggregation, induced by ADP (20 µmol/ml), decreased by 42±10% ($p<0.03$). In addition, the platelet aggregation produced by the combination of epinephrine and ADP was decreased by 32±11% ($p<0.05$) after PROVEXCV2™ administration.

In humans, the effects of PROVEXCV2 on platelet activity also was evaluated ex vivo using the whole blood platelet aggregometry test. Specifically, twelve healthy human volunteers (8 men, 4 women) aged 22–50 years of age were recruited. They abstained from tea, alcoholic beverages, grape products, flavonoid and vitamin supplements, and all medications including aspirin products for one week prior to and throughout the study. Vegetarians were excluded from the study.

On day 1 of the study for each volunteer, 18 ml of venous blood was drawn for the ex vivo whole blood platelet aggregometry test, between 8 am and 12 noon while in the fasting state. Then, each volunteer was instructed to consume 5–7 capsules (about 20/mg/kg/day), depending on their body weight, of PROVEXCV2™ for 7–14 days. After 7–14 days, each volunteer returned to the laboratory in the fasting state, but having taken that day's dose of PROVEXCV2™, and had a second blood sample drawn. This sample was drawn about 2–4 hours after the last dose of PROVEXCV2™.

Briefly, 18 ml of whole blood was drawn into a syringe containing 2 ml of 3.8% sodium citrate as an anticoagulant. The blood was immediately diluted with an equal volume of preservative-free saline. One milliliter (1 ml) of the diluted blood was placed in a cuvette with a siliconized stir bar and warmed to 37° C. for 5 minutes. An electrode is placed in the cuvette to measure the impedance change, which is proportional to the platelet aggregation. Once the baseline platelet activity was recorded, a high dose of collagen (12.5 µg) was added to the pre-warmed blood and placed in the aggregometer to obtain a maximum platelet aggregation response. The change in impedance produced by platelet aggregation was followed for 7 minutes. Sub-maximal doses of collagen (0.5 µg/ml), phorbol 12-myristate 13-acetate (PMA) (0.5 nmol/ml), and ADP (20 µmol/ml) were used as platelet agonists. In addition, ADP (20 µmol/ml) was also used as an agonist to aggregate platelets in 1 ml of blood pre-incubated for 1 minute with epinephrine (0.5 µg/ml). The aggregation responses were measured in duplicate in the control sample and compared to the responses after 7–14 days of daily PROVEXCV2™.

The platelet aggregation response to collagen (0.5 µg/ml), ADP (20 µmol/ml), and a phorbol ester, phorbol 12-myristate 13-acetate (PMA; 0.5 nmol/ml), in the samples collected after 7–14 days of daily PROVEXCV2™ administration revealed a reduction of 51.6±41.1% (p<0.005), 39.8±41.5% (p<0.005), and 17.9±10.0% (p<0.002), respectively. In addition, the platelet aggregation in response to a combination of epinephrine (0.5 µg/ml) and ADP (20 µmol/ml) in the samples collected after 7–14 days of daily PROVEXCV2™ administration revealed a reduction of 14.9±8.5% (p<0.05). These results suggest that the mechanism of platelet activity inhibition by PROVEXCV2™ may be through the inhibition of platelet protein kinase C since PMA induced platelet aggregation was reduced after 7–14 days of daily PROVEXCV2™ administration.

In addition to evaluating the effects of PROVEXCV2™ on platelet activity, the effects of PROVEXCV2™ on LDL cholesterol oxidation was studied. Briefly, LDL was isolated from serum collected from a healthy-fasting volunteer using sequential ultra-centrifugation with spins at densities of 1.006 g/ml to remove VLDL/chylomicrons and 1.063 g/ml (KBr) to recover the LDL from the denser HDL and serum proteins. The duration of each spin was 3 hours using a Beckman Optima set at 100,000 rpms (>4,000,000× g). The LDL was dialyzed against phosphate buffered saline (PBS) containing EDTA for 48 hours with several changes of the buffer. The dialyzed material was then checked by electrophoresis (agarose gel) to demonstrate the absence of other lipoproteins fractions or serum proteins. The protein concentration of the isolated LDL was measured and adjusted to 0.5 g/L using EDTA-containing PBS for dilutions. The LDL solution was then aliquoted in 0.7 ml volumes into small glass containers with screw caps enclosures. The vials and the LDL solutions were flushed with nitrogen to remove traces of oxygen to ensure stability and stored at −80° C. until just prior to use.

LDL oxidation was performed as described above. Briefly, the LDL was diluted with EDTA-free PBS by mixing 100 µl of thawed LDL with 900 µl of PBS just prior to the oxidizability study. Ten (10) µl of freshly prepared $CuCl_2$ (final concentration of 5 µmol/L) was added to the LDL solution to initiate oxidation. The rate of formation of conjugated dienes was monitored spectrophotometrically at 234 nm at 30° C. for 5 hours taking absorbance readings every 3 minutes. The spectrophotometer is equipped with a six place automatic sample holder to provide a maximum of six specimens analyzed in a single run. LDL alone with PBS and $CuCl_2$ is used as a control when assessing the ability of PROVEXCV2™ using direct mixing in vitro experiments.

The time course of LDL oxidation shows three consecutive phases: a lag phase in which there is hardly any conjugated diene formation, a propagation phase with a rapid increase in diene formation, and finally a decomposition phase. The lag phase, defined as the time period between the addition of $CuCl_2$ and the start of propagation, is considered to reflect the LDL's susceptibility to oxidative stress.

Figure 8:
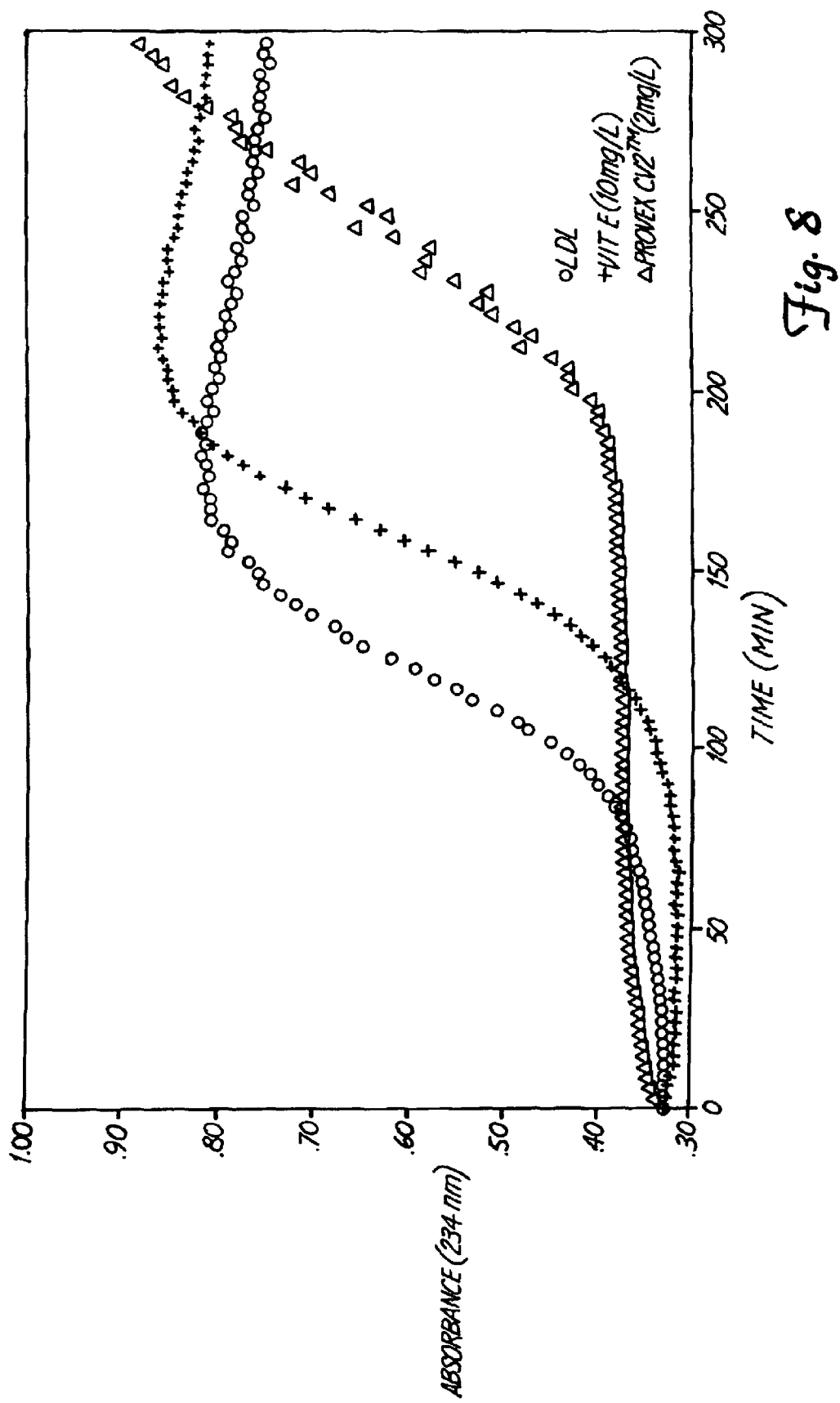
FIG. 8 is a graph depicting the rate of LDL cholesterol oxidation.

The rate of production of conjugated dienes in a sample of LDL cholesterol is shown in FIG. 8. Native LDL cholesterol was compared to an equal sample of LDL cholesterol incubated with Vitamin E (5.3 mg/L) or with PROVEXCV2™ (1.0 mg/L). The lag time before oxidation begins was delayed by vitamin E and delayed to a significantly greater extent by PROVEXCV2™. This result indicates that PROVEXCV2™ is a more potent antioxidant than Vitamin E, when exposed to copper ion enhanced oxidation.

Other aspects, advantages, and modifications are within the scope of the following claims.

What is claimed is:

1. A dietary supplement for inhibiting platelet aggregation, said supplement comprising effective amounts of a grape seed extract, a grape skin extract, and an enzyme, wherein said supplement comprises 3.3 percent or more of said grape seed extract by weight, wherein said grape seed extract and said grape skin extract each contain one or more flavonoids, and wherein said enzyme is selected from the group consisting of a fungal protease, an acid stable protease, and bromelain.

2. The supplement of claim 1, wherein said supplement is in the form of a pill, powder, or tablet.

3. The supplement of claim 1, wherein said supplement further comprises a bilberry extract.

4. The supplement of claim 1, wherein said supplement further comprises a ginkgo biloba extract.

5. The supplement of claim 1, wherein said supplement further comprises quercetin.

6. The supplement of claim 1, wherein said supplement comprises about 24 percent or less of said enzyme by weight.

7. The supplement of claim 1, wherein said supplement further comprises a ginkgo biloba extract, a bilberry extract, quercetin, a fungal protean, an acid stable protease, and bromelain.

8. The supplement of claim 7, wherein said supplement comprises about 12 percent of said grape seed extract by weight, about 20 percent of said grape skin extract by weight, about 10 percent of said ginkgo biloba extract by weight, about 10 percent of said bilberry extract by weight, about 24 percent of said quercetin by weight, and about 24 percent of an enzyme blend by weight.

9. The supplement of claim 7, wherein said supplement comprises about 3.30 percent of said grape seed extract by weight, about 67.77 percent of said grape skin extract by weight, about 9.71 percent of said ginkgo biloba extract by weight, about 7.32 percent of said bilberry extract by weight, about 7.32 percent of said quercetin by weight, and about 4.58 percent of art enzyme blend by weight.

10. A dietary supplement for inhibiting platelet aggregation, said supplement comprising effective amounts of a grape seed extract, a grape skin extract, and an enzyme, wherein said supplement comprises 32 percent or more of said grape seed extract and said grape skin extract by weight, wherein said grape seed extract and said grape skin extract contain one or more flavonoids, and wherein said enzyme is selected from the group consisting of a fungal protease, an acid stable protease, and bromelain.

11. The supplement of claim 10, wherein said supplement is in the form of a pill, powder, or tablet.

12. The supplement of claim 10, wherein said supplement further comprises a bilberry extract.

13. The supplement of claim 10, wherein said supplement further comprises a ginkgo biloba extract.

14. The supplement of claim 10, wherein said supplement further comprises quercetin.

15. The supplement of claim 10, wherein said supplement comprises about 24 percent or less of said enzyme by weight.

16. The supplement of claim 10, wherein said supplement further comprises a ginkgo biloba extract, a bilberry extract, quercetin, a fungal protease, an acid stable protease, and bromelain.

17. The supplement of claim 16, wherein said supplement comprises about 12 percent of said grape seed extract by weight, about 20 percent of said grape skit extract by weight, about 10 percent of said ginkgo biloba extract by weight, about 10 percent of said bilberry extract by weight, about 24 percent of said quercetin by weight, and about 24 percent of an enzyme blend by weight.

18. The supplement of claim 16, wherein said supplement comprises about 3.30 percent of said grape seed extract by weight, about 67.77 percent of said grape skin extract by weight, about 9.71 percent of said ginkgo biloba extract by weight, about 7.32 percent of said bilberry extract by weight, about 7.32 percent of said quercetin by weight, and about 4.58 percent of an enzyme blend by weight.

19. A method for inhibiting platelet aggregation in a mammal in need thereof, wherein said method comprises administering a supplement comprising effective amounts of a grape seed extract, a grape skin extract, and an enzyme, wherein said grape seed extract and said grape skin extract contain one or more flavonoids, wherein said enzyme is selected from the group consisting of a fungal protease, an acid stable protease, and bromelain, and wherein:

(a) said supplement comprises 3.3 percent or more of said grape seed extract by weight, or (b) said supplement comprises 32 percent or more of said grape seed extract and said grape skin extract by weight.

20. The method of claim 19, wherein said supplement is in the form of a pill, powder, or tablet.

21. The method of claim 19, wherein said supplement further comprises a fungal protease, an acid stable protease, and bromelain.

22. The method of claim 19, wherein said supplement further comprises a bilberry extract.

23. The method of claim 19, wherein said supplement further comprises a ginkgo biloba extract.

24. The method of claim 19, wherein said supplement further comprises quercetin.

25. The method of claim 19, wherein said supplement comprises about 24 percent or less of said enzyme by weight.

26. The method of claim 19, wherein said supplement further comprises a ginkgo biloba extract, a bilberry extract, quercetin, a fungal protease, an acid stable protease, and bromelain.

27. The supplement of claim 26, wherein said supplement comprises about 12 percent of said grape seed extract by weight, about 20 percent of said grape skin extract by weight, about 10 percent of said ginkgo biloba extract by weight, about 10 percent of said bilberry extract by weight, about 24 percent of said quercetin by weight and about 24 percent of an enzyme blend by weight.

28. The supplement of claim 26, wherein said supplement comprises about 3.30 percent of said grape seed extract by weight, about 67.77 percent of sail grape skin extract by weight, about 9.71 percent of said ginkgo biloba extract by weight, about 7.32 percent of said bilberry extract by weight, about 7.32 percent of said quercetin by weight, and about 4.58 percent of an enzyme blend by weight.

* * * * *

UNITED STATES PATENT AND TRADEMARK OFFICE
CERTIFICATE OF CORRECTION

PATENT NO. : 6,818,233 B2  Page 1 of 1
DATED : November 16, 2004
INVENTOR(S) : Lynn Perkes It is certified that error appears in the above-identified patent and that said Letters Patent is hereby corrected as shown below:

Title page,
Item [56], References Cited, OTHER PUBLICATIONS,
"Folts, J.D." third reference, after "(1996)", please insert -- Abstract No. 457 --;
"Beretz et al." reference, please delete "(abstract only)";
"Goker et al." reference, please delete "(abstract only)";
"Hertog et al." reference, please delete "(abstract only)";
"Hladovec et al." reference, please delete "(abstract only)";
"Huang et al." reference, please delete "(abstract only)";
"Jahromi and Ray" reference, please delete "(abstract only)";
"Keli et al." reference, please delete "(abstract only)";
"Knekt et al." reference, please delete "(abstract only)";
"Littlewood et al." reference, please delete "(abstract only)";
"Monforte et al." reference, please delete "(abstract only)";
"Robak et al." reference, please delete "(abstract only)";
"Smith et al." reference, please delete "(abstract only)";
"Taussig and Batkin" reference, please delete "(abstract only)";
"Vellini et al." reference, please delete "(abstract only)";

Column 16,
Line 24, please delete "protean" and insert -- protease -- therefor;
Line 39, please delete "art" and insert -- an -- therefor;
Line 66, please delete "skit" and insert -- skin -- therefor;

Column 18,
Line 19, after "weight" please insert -- , --;
Line 23, please delete "sail" and insert -- said -- therefor.

Signed and Sealed this

Twenty-fourth Day of May, 2005

JON W. DUDAS
*Director of the United States Patent and Trademark Office*